(12) United States Patent
Monassevitch et al.

(10) Patent No.: US 6,402,765 B1
(45) Date of Patent: Jun. 11, 2002

(54) SURGICAL CLIP

(75) Inventors: Leonid Monassevitch, Givat Olga; Shlomo Lelcuk, Savlon; Michael Arad, Tel-Aviv, all of (IL)

(73) Assignee: Niti Alloys Technologies Ltd., Netanya (IL)

( * ) Notice: Subject to any disclaimer, the term of this patent is extended or adjusted under 35 U.S.C. 154(b) by 154 days.

(21) Appl. No.: 09/592,518

(22) Filed: Jun. 12, 2000

(51) Int. Cl.$^7$ ............................................ A61B 17/08
(52) U.S. Cl. ..................................................... 606/151
(58) Field of Search .................... 606/151, 153, 606/155–158, 213, 215, 216, 188, 219, 221, 78

(56) References Cited

U.S. PATENT DOCUMENTS

| | | | |
|---|---|---|---|
| 5,171,252 A | | 12/1992 | Friedland |
| 5,176,544 A | * | 1/1993 | AbuJudom, II et al. .... 439/878 |
| 6,088,889 A | * | 7/2000 | Luther et al. .................. 24/489 |
| 6,171,320 B1 | * | 1/2001 | Monassevitch ............. 606/151 |
| 6,206,913 B1 | * | 3/2001 | Yencho et al. ................ 623/1.3 |
| 6,254,615 B1 | * | 7/2001 | Bolduc et al. ............... 606/142 |

FOREIGN PATENT DOCUMENTS

| | | |
|---|---|---|
| EP | 0 326 757 | 7/1993 |
| SU | 1186199 | 10/1985 |

* cited by examiner

Primary Examiner—Michael J. Milano
Assistant Examiner—Daniel Jacob Davis
(74) Attorney, Agent, or Firm—Pearne & Gordon LLP (57) ABSTRACT

A surgical clip and method for anastomosing a gastrointestinal tract, the clip being formed at least partly of a shape memory alloy, the clip including: a first length of a wire defining a closed geometrical shape having a central opening; a second length of a wire defining a closed geometrical shape similar in configuration and magnitude to that of the first length of wire, wherein, when placed in side-by-side registration, the first and second lengths of wire fully overlap; an intermediate portion located between the first length of wire and the second length of wire, the intermediate portion formed of a shape memory alloy; a cutting element associated with the first length of wire; a counter element associated with the second length of wire and arranged for cutting engagement with the cutting element; wherein when at a first temperature or higher, the first and second lengths of wire are positioned in a side-by-side closed position and the shape memory alloy is in an elastic state, and further, when at a second temperature or lower, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-by-side closed position, thereby to apply a compressive force to tissue located therebetween.

13 Claims, 9 Drawing Sheets

FIG.7D ial clips
SURGICAL CLIP

FIELD OF THE INVENTION

The present invention relates to the field of surgical clips generally, and, in particular, to the field of surgical clips formed of a shape memory alloy.

BACKGROUND OF THE INVENTION

Several methods are known in the art for joining portions of hollow organs, such as the gastrointestinal tract. These include threads for manual suturing, staplers for mechanical suturing, and compression rings and clips.

While manual suturing is universally known and relatively inexpensive, the degree of success depends considerably on the skill of the surgeon. Another disadvantage is that post-operative complications are common. Further, suturing an organ results in lack of smoothness of the tissue therein, which, when the sutured organ is part of the gastrointestinal tract, hampers peristalsis in the sutured area. Finally, suturing is both labor and time consuming.

Staplers for mechanical suturing ensure a reliable joining of tissue and enable the time needed for surgery to be reduced, compared with manual suturing. However, due to the facts that such staples are not reusable and that a great many types and sizes are required, the price of staples is high. Also, after healing, metal staples remain in place along the perimeter of the which reduces elasticity of the junction and adversely affects peristalsis when the sutured organ is part of the gastrointestinal tract.

Junctions using compression devices such as rings and clips ensure the best seal and post-operative functioning of the organs. Two types of compression devices are known, namely, rings made of resorption plastics and clips made of memory alloys. Plastic rings are cumbersome and expensive. Also, the compression force is applied only momentarily at the junction and is reduced as the tissue is crushed. Clips made of shape memory alloys enable portions of tissue to be pressed together when equilibrium with body temperature is reached, whereat, due to the inherent properties of the alloys, the clips resume their memorized shape.

Development of clips made of memory alloy materials has increased recently, as they have many advantages over other devices. Their design is simple, they are cheap, they are small in size and possess universal qualities, and they are self-evacuated from the gastrointestinal tract.

It is known in the art to provide a surgical fastening clip which applies a clamping force to a site, such as a blood vessel, thereby reducing its cross-sectional area. It is also known to provide a surgical fastening clip formed of a shape memory alloy which deforms to a closed configuration when heated, such that the clamping force applied thereby is increased as it is heated. For example, U.S. Pat. No. 5,171,252 discloses a surgical fastening clip formed of a shape memory alloy; the device disclosed therein includes separate legs which close tightly around a site. Such a device is limited in its uses, such as for clamping blood vessels, and is not suitable for joining portions of the gastrointestinal tract.

EP 0,326,757 discloses a device for anastomosing a digestive tract, which includes a plurality of U-shaped retaining clips disposed around a soluble support tube. The tube is positioned inside portions of the digestive tract to be joined, and includes an outer groove around which are disposed the U-shaped retaining clips. The retaining clips are made of a shape memory alloy such that the open ends thereof close at a predetermined temperature, thus joining ends of the digestive tract. Once the ends of the digestive tract have been joined, the tube is dissolved. Such a device is disadvantageous in that its use requires that a plurality of clips to be properly positioned simultaneously. Also, there is no assurance that the resulting junction will be smooth, due to the plurality of sites of the digestive tract joined by the plurality of clips.

SU 1,186,199 discloses a memory alloy clip consisting of two parallel coils to be used for joining portions of a hollow organ, such as an organ of the gastrointestinal tract. The portions of the organ to be joined are aligned, and each of the plastic coils is introduced through a puncture formed in the wall of one of the portions. The coils are positioned such that, when heated, they compress the aligned walls therebetween, thus maintaining the portions of the walls held within the loops of the coils adjacent each other. Thereafter, incisions are made through the portions of the walls held within the loops of the coils, such that a passageway is created between the two organ portions. The punctures in the organ walls must then be surgically sewn closed with interrupted surgical sutures.

A major disadvantage of known memory alloy clips is that they permit compression of only approximately 80–85% of the junction perimeter, thus requiring additional manual sutures, which reduce the seal of the junction during the healing period and its elasticity during the post-operative period. Also, this additional suturing is problematic inasmuch as it has to carried out across a joint which includes a portion of the clip, thereby rendering difficult the sealing and anastomosis of the organ portions. Furthermore, once in place, clips according to the prior art require further surgery to be performed, namely, incisions through tissue so as to create a passageway between the two organ portions which have been joined by the clip.

There is thus a need for a surgical device which facilitates compression of substantially the entire perimeter of the junction between the organ portions being joined, which would obviate the need for additional manual sutures and which ensure the smooth seal of the junction during the healing period and its elasticity during the post-operative period. Additionally, there is a need for a surgical device which, once in place, would enable a passageway to be created between the two organ portions which have been joined together, without requiring further surgery to be performed on the organ.

SUMMARY OF THE INVENTION

The present invention seeks to provide an improved surgical clip formed of a shape memory alloy, and a method of joining two portions of a hollow organ, which overcome disadvantages of prior art.

There is thus provided, in accordance with a preferred embodiment of the present invention, a surgical clip formed at least partly of a shape memory alloy, the clip including: a first length of a wire defining a closed geometrical shape having a central opening; a second length of a wire defining a closed geometrical shape similar in configuration and magnitude to that of the first length of wire, wherein, when placed in side-by-side registration, the first and second lengths of wire fully overlap; an intermediate portion located between the first length of wire and the second length of wire, the intermediate portion formed of a shape memory alloy; a cutting element associated with the first length of wire; a counter element associated with the second length of wire and arranged for cutting engagement with the cutting element; wherein when at a first temperature or higher, the first and second lengths of wire are positioned in a side-by-side closed position and the shape memory alloy is in an elastic state, and further, when at a second temperature or lower, below the first temperature, the shape memory alloy is in a plastic state, thereby enabling the first and second lengths of wire to be moved into and to retain a spaced apart position, and upon heating of the clip to a temperature at least equal to the first temperature, the first and second lengths of wire return to the side-by-side closed position, thereby to apply a compressive force to tissue located therebetween.

Additionally in accordance with a first embodiment of the present invention, the surgical clip further includes apparatus for pressing the cutting element into cutting engagement with the counter element wherein, when at the first temperature or higher, the apparatus for pressing presses the cutting element into cutting engagement with the counter element.

In accordance with an alternative embodiment of the present invention, the surgical clip further includes apparatus for pressing the cutting element into cutting engagement with the counter element wherein, when at the first temperature or higher, the apparatus for pressing is actuatable by an outside force.

Further in accordance with an embodiment of the present invention, the geometrical shape of the surgical clip is a circle.

Yet further in accordance with an alternative embodiment of the present invention, the geometrical shape of the surgical clip is an ellipse.

In accordance with an embodiment of the present invention, the first length of wire and the second length of wire are defined by a continuous coil.

Still further in accordance with an alternative embodiment of the present invention, the first length of wire and the second length of wire are two distinct lengths of wire, each defining a closed geometrical shape.

Still further in accordance with a preferred embodiment of the present invention the counter element also includes a cutting element.

According to the present invention, there is also provided a method for anastomosing a gastrointestinal tract, the method including the following steps: (a) providing a surgical clip formed at least partly of a shape memory alloy, the clip including: a first length of a wire defining a closed geometrical shape having a central opening; a second length of a wire defining a closed geometrical shape similar in configuration and magnitude to that of the first length of wire, wherein, when placed in side-by-side registration, the first and second lengths of wire fully overlap; an intermediate portion located between the first length of wire and the second length of wire, the intermediate portion formed of a shape memory alloy; a cutting element associated with the first length of wire; a counter element associated with the second length of wire and arranged for cutting engagement with the cutting element; (b) cooling at least the intermediate portion to a temperature below a lower phase transition temperature thereof, whereat the intermediate portion is in a plastic state, thereby enabling the first and second lengths of wire to be moved into and to retain a spaced apart position; (c) manually moving apart the first and second lengths of wire; (d) drawing together portions of the gastrointestinal tract wherein anastomosis is desired, such that the portions are in adjacent, side-by-side relationship, at least one of the portions being open-ended; (e) surgically sealing the open ends of the portions of the gastrointestinal tract; (f) forming punctures in walls of the gastrointestinal tract adjacent to each other, the puncture being adjacent; (g) introducing the clip through the punctures, such that the a wall of each portion of the gastrointestinal tract is situated between the first and second lengths of wire; (h) maintaining the relative positions of the portions of the gastrointestinal tract and the clip in relation thereto, while raising the temperature of at least the intermediate portion to a temperature above its upper phase transition temperature, whereat the intermediate portion is in an elastic state, thereby causing the first and second lengths of wire to attain the side-by-side registration, thereby to apply a compressive force to tissue located therebetween.

Additionally in accordance with a preferred embodiment of the present invention, according to the method, in step (h), the temperature of the clip is raised to the temperature above its upper phase transition temperature by the heat of the gastrointestinal tract.

Further in accordance with a preferred embodiment of the present invention, according to the method, the clip further including apparatus for pressing the cutting element into cutting engagement with the counter element wherein, when at the upper phase transition temperature or higher, the apparatus for pressing presses the cutting element into cutting engagement with the counter element, thereby creating an opening in the tissue located between the first and second lengths of wire, thereby creating initial patency of the gastrointestinal tract; and the method includes after step (h), the additional step of widening the opening.

BRIEF DESCRIPTION OF THE DRAWINGS

The present invention will be more fully understood and appreciated from the following detailed description, in which.

DETAILED DESCRIPTION OF THE INVENTION

The present invention seeks to provide a surgical clip, formed at least partly of a shape memory alloy, such as is known in the art, and which provides organ tissue compression along the entire periphery of the clip, thereby to ensure satisfactory joining or anastomosis of portions of an organ, and which provides apparatus for cutting a portion of tissue, whereby initial patency of the gastrointestinal tract is created. The present invention further seeks to provide a method for performing anastomosis of organ portions, such as those of the gastrointestinal tract, the method employing the clip of the present invention, and for cutting a portion of tissue, whereby initial patency of the gastrointestinal tract is created.

Figure 1A:
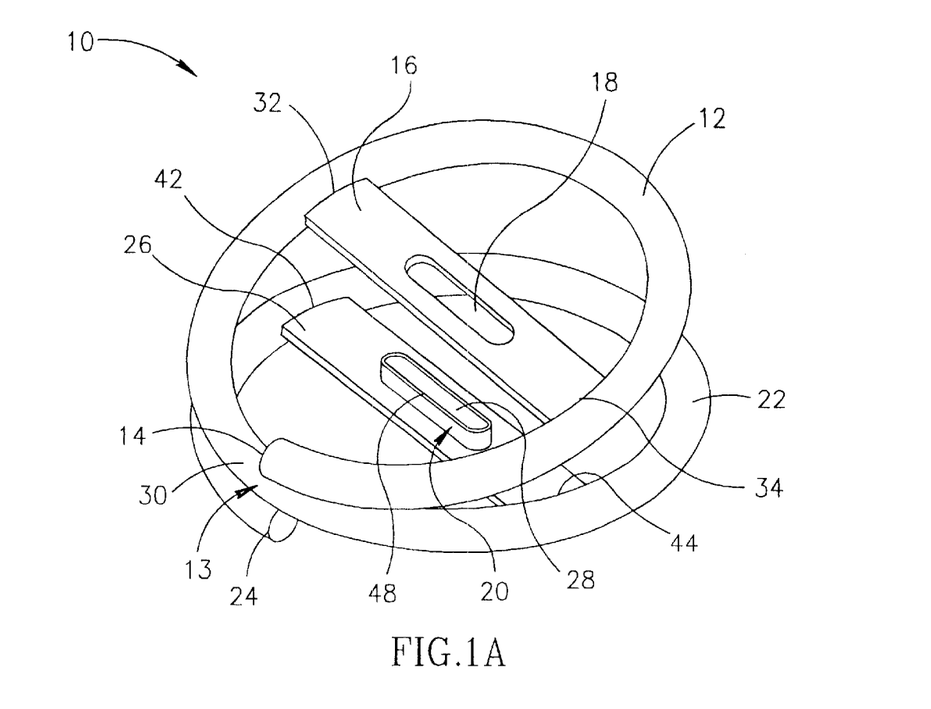
FIGS. 1A and 1B are pictorial illustrations of a surgical clip according to a first embodiment of the present invention, the clip being in an open configuration and a closed configuration, respectively.
Figure 1B:
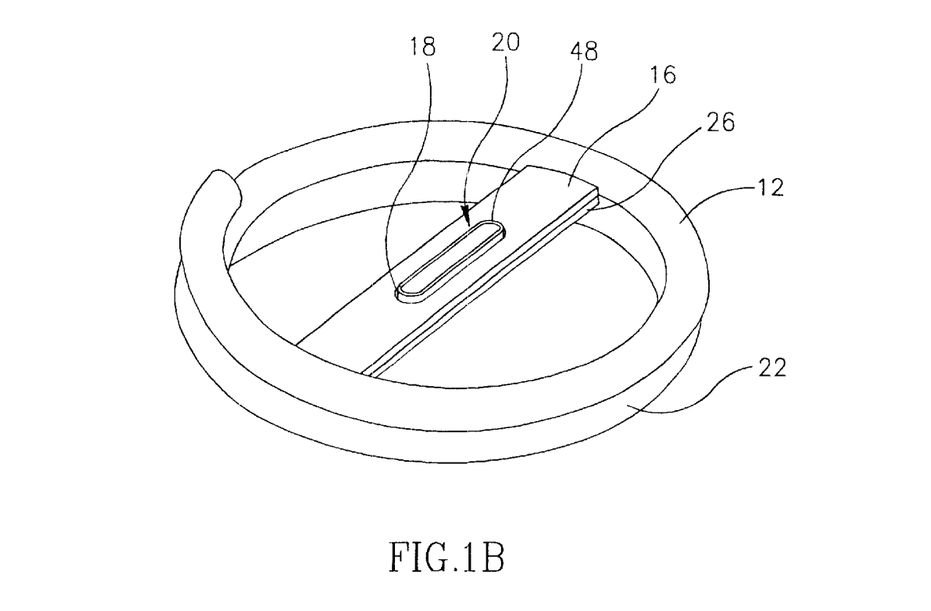

Referring now to the drawings, FIGS. 1A and 1B illustrate a surgical clip, referenced generally 10, according to a first embodiment of the present invention, the clip 10 shown in respective open and closed configurations. Clip 10 is typically wire-like, formed at least partly of a shape memory alloy, and is of a coiled configuration so as to include a pair of loops 12 and 22, having respective ends 14 and 24. Each of loops 12 and 22 defines a complete circle from its end to a point 30 midway along the coil. Thus, the coil defines two complete circles from end 14 of loop 12 to end 24 of loop 22. While the various embodiments of the clip of the present invention are illustrated as defining circular shapes, it will be appreciated by persons skilled in the art that the present invention may, alternatively, define any closed geometric shape, such as an ellipse.

At least an intermediate portion 13 of clip 10 is formed of a shape memory alloy such that, when cooled to below a predetermined temperature, the clip is in a plastic state, such that loops 12 and 22 may be moved apart, as to the position shown in FIG. 1A. When heated to above the predetermined temperature, the clip 10 is in an elastic state, such that the loops 12 and 22 are adjacent each other, as in the position shown in FIG. 1B. The change in temperature, as it affects the shape memory alloy, will be discussed further, with reference to FIGS. 7A–D.

Loops 12, 22 of clip 10 are provided with a pair of crossbars 16, 26, respectively, which extend across respective loops 12, 22. Crossbars 16 and 26 may be fastened to respective loops 12 and 22 by any suitable means. Crossbar 16 is provided with an aperture 18, and crossbar 26 is provided with a hollow cutting element 20 having a blade portion 48 which circumscribes an aperture 28. Blade portion 48 of cutting element 20 has a configuration and size relative to aperture 18 so as fit snugly therein (FIG. 1B). Crossbar 16 extends between points 32 and 34 along the circle defined by loop 12, and crossbar 26 extends between points 42 and 44 along the circle defined by loop 22. The distance along loop 12 from point 30 to point 32 is the same as the distance along loop 22 from end 24 to point 42. Similarly, the distance along loop 12 from end 14 to point 34 is the same as the distance along loop 22 from point 30 to point 44. Thus, as shown in FIG. 1B, when loops 12 and 22 are adjacent, crossbars 16 and 26 overlie each other, and cutting element 20 is aligned with aperture 18. While crossbars 16 and 26 are shown at a particular orientation relative to loops 12 and 22, respectively, it will be appreciated by persons skilled in the art that any orientation whereby crossbars 16 and 26 overlie each other is possible, without departing from the scope of the invention.

As shown in FIG. 1B, when in the closed configuration, loops 12 and 22 are adjacent to each other, crossbars 16 and 26 are adjacent to each other, and cutting element 20 is positioned snugly within aperture 18. The crossbar 16 thus acts as a counter element for cutting element 20.

Figure 2A:
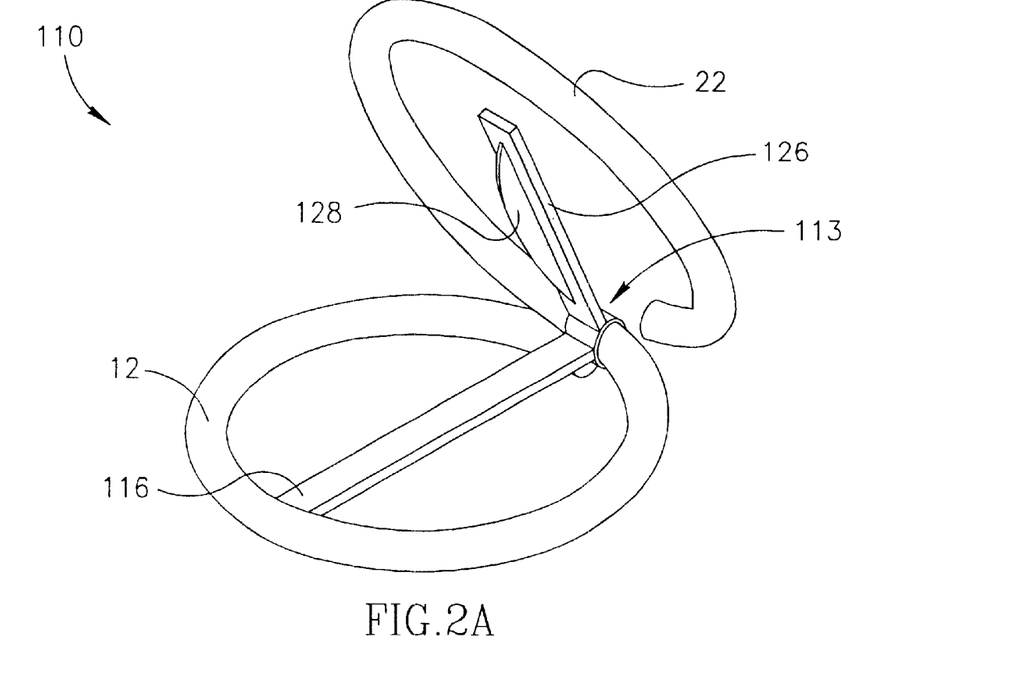
FIGS. 2A and 2B are pictorial illustrations of a surgical clip according to a second embodiment of the present invention, the clip being in an open configuration and in a closed configuration, respectively.
Figure 2B:
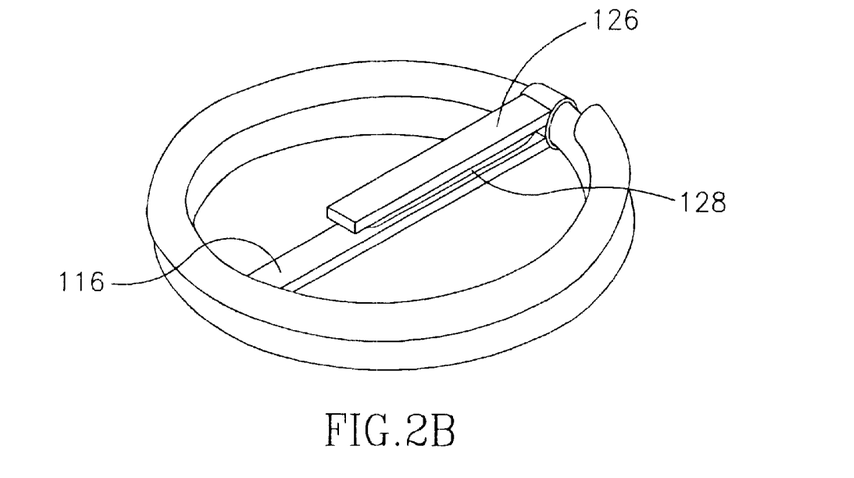

With reference to FIGS. 2A and 2B, there is shown a surgical clip, referenced generally 110, according to a second embodiment of the present invention, the clip being in an open configuration and in a closed configuration, respectively. Clip 110 is similar to clip 10 (FIGS. 1A, 1B) in that it defines a coil of two complete circles, including an intermediate portion 113 formed of a shape memory alloy, but clip 110 is provided with a crossbar 116 and bar 126 on respective loops 112, 122. Crossbar 116 and bar 126 may be fastened to respective loops 12 and 22 by any suitable means. Bar 126 is also provided with a surgical blade 128 which extends out of bar 126 such that, when the clip 110 is in the closed configuration, blade 128 presses against crossbar 116. Thus, crossbar 116 acts as a counter element for blade 128.

FIGS. 3A–D illustrate a surgical clip, referenced generally 130, according to a third embodiment of the present invention. Clip 130 includes an intermediate portion 13 formed of a shape memory alloy and defines a coil of two complete circles, as does clip 10, and has similar loops 12 and 22. However, in this embodiment of the present invention, loop 22 of clip 130 is provided with a cutting element 133 in the form of an L-shaped arm 132 having a blade 134 at its end which extends towards the center of loop 22. Loop 12 is provided with a counter element 136 in the form of an arm 137 having a U-shaped portion 138 at its end, the open end of the U facing towards the center of loop 12. L-shaped element 132 and counter element 136 may be fastened to respective loops 22 and 12 by any suitable means. It will be appreciated by persons skilled in the art that cutting element 133 and arm 132 may be configured as having any other suitable shapes whereby they will function as a cutting element and counter element for the purposes of the present invention.

Figure 3A:
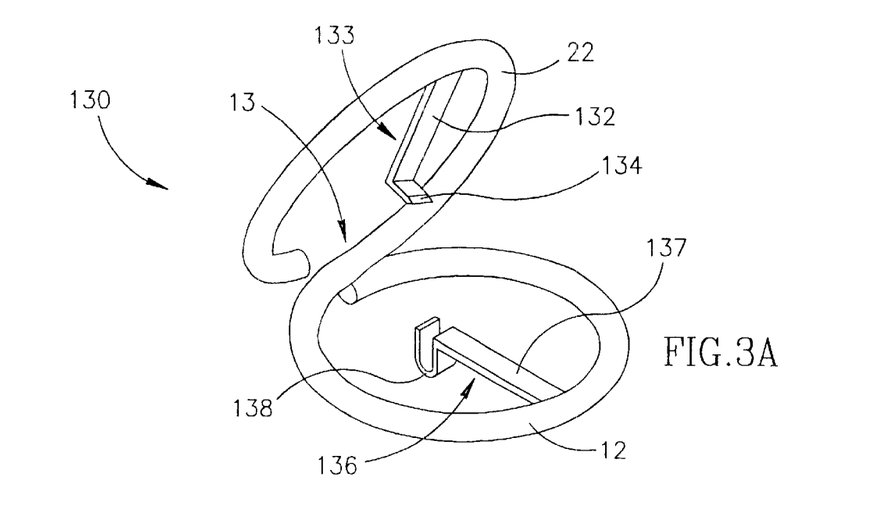
FIG. 3A is a pictorial illustration of a surgical clip according to a third embodiment of the present invention, the clip being in an open configuration.
Figure 3B:
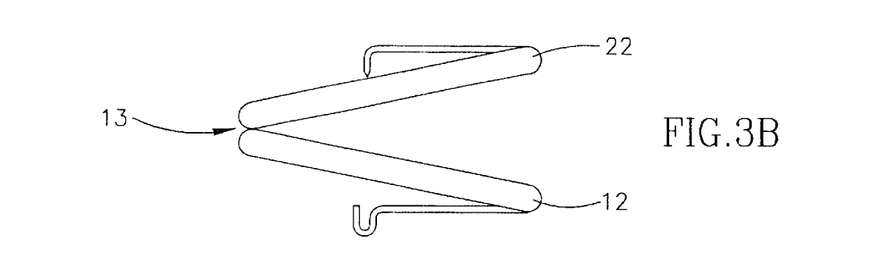
FIG. 3B is a side view of the surgical clip shown in FIG. 3A.
Figure 3C:
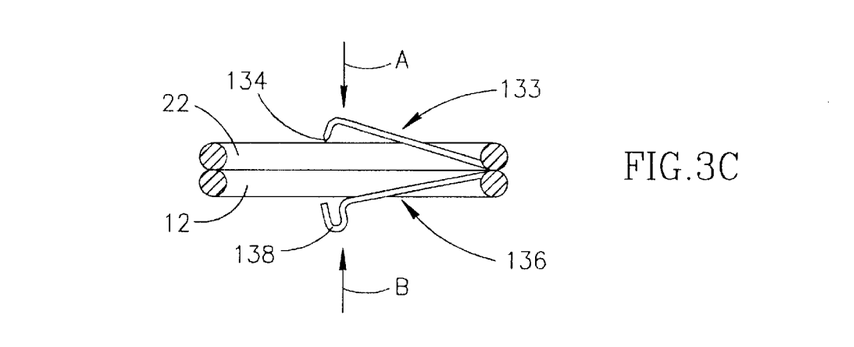
FIG. 3C is a side view of the surgical clip shown in FIG. 3B, the clip being in a closed configuration.
Figure 3D:
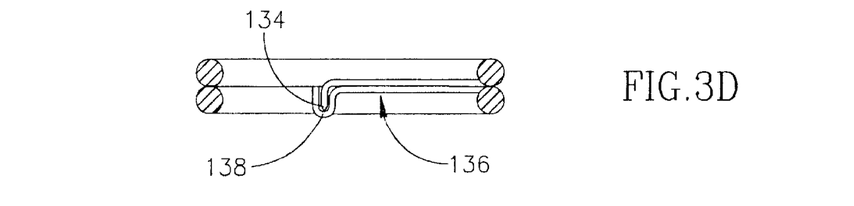
FIG. 3D is a side view of the surgical clip shown in FIG. 3C, wherein the cutting element and counter element are being pressed against each other.

FIGS. 3A–B shows clip 130 with intermediate portion 13 in a plastic state, wherein the loops 12 and 22 have been moved apart. When intermediate portion 13 is in an elastic state, as shown in FIGS. 3C–D, loops 12 and 22 are pressed against each other. As shown in FIG. 3C, blade 134 of cutting element 133 is positioned adjacent yet apart from U-shaped portion 138 of counter element 136. By manually applying external pressure to both cutting element 133 and counter element 136, in the direction of arrows A and B, respectively, these elements are forced together such that they make contact, as shown in FIG. 3D, blade 134 being pressed against counter element 136 at approximately the center of the U-shaped portion 138 thereof. After release of cutting element 133 and counter element 136, these elements are allowed to return to their positions shown in FIG. 3C.

FIGS. 4A, 4B, 4C, and 4D illustrate a surgical clip, referenced generally 140, according at to a fourth embodiment of the present invention. Clip 140 includes two ring portions 142, 144, which are attached at an intermediate portion 150. While, if desired, the entire clip 140 may be formed of a shape memory alloy, it is essential that at least the intermediate portion 150 be formed of a shape memory alloy. Ring portions 142 and 144 are provided with respective crossbars 146 and 148. At the center of crossbar 146 there is provided a cutting element 152 which is slidably attached therethrough. Cutting element 152 includes a ring-shaped head portion 156 and a cylindrical portion 158 having an aperture 159. Crossbar 148 is provided with a counter element 162 in the form of a cylindrical aperture 154, of size and configuration similar to that of cylindrical portion 158 of cutting element 152, and of a flange portion 160 (FIGS. 4B, 4C, 4D), positioned about aperture 154 on the side of crossbar 148 which is distal to crossbar 146.

While the cutting element 152 and counter element 162 of clip 140 are shown as having a particular size and shape, it will be appreciated by persons skilled in the art that any suitable configuration of cutting element and counter element may be employed, whereby tissue located therebetween may be sliced or cut out.

Figure 4A:
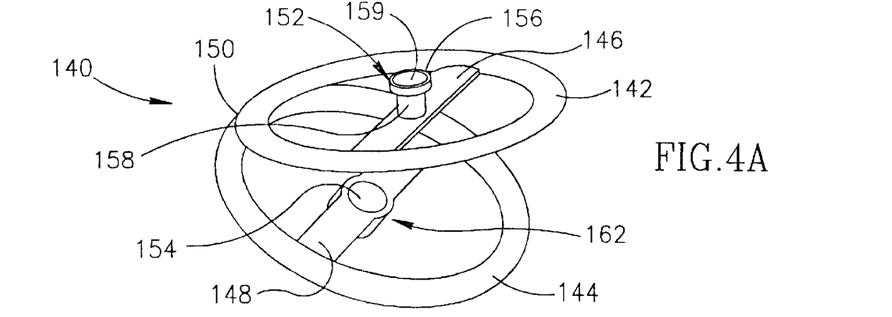
FIGS. 4A and 4B are respective pictorial and side view illustrations of a surgical clip according to a fourth embodiment of the present invention, the clip being in an open configuration.
Figure 4B:
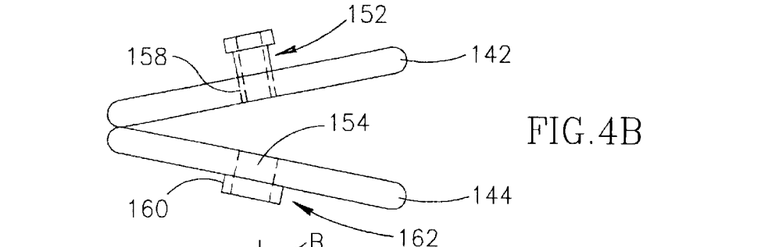
Figure 4C:
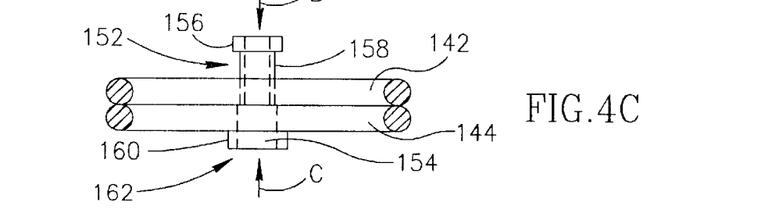
FIG. 4C is a side view of the surgical clip shown in FIG. 4A, the clip being in a closed configuration.
Figure 4D:
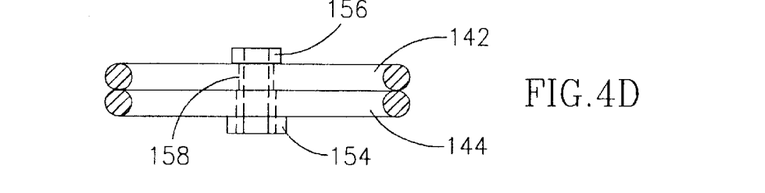
FIG. 4D is a side view of the surgical clip shown in FIG. 4C, wherein the cutting element and counter element are being pressed together.

In FIGS. 4A–B, intermediate portion 150 of clip 140 is shown in its plastic state, wherein ring portions 142 and 144 have been moved apart. When intermediate portion 150 of the clip 140 is in an elastic state, as shown in FIGS. 4C–D, ring portions 142 and 144 are firmly pressed against each other, and cylindrical portion 158 of cutting element 152 is positioned adjacent aperture 154 of counter element 162. By applying pressure to head portion 156 of cutting element 152 on crossbar 146, in the direction of arrow B, and to flange portion 160 on counter element 162, in the direction of arrow C, cylindrical portion 158 is forced into aperture 154, where it is held in position by the snug fit between cylindrical portion 158 and the inner surface of aperture 154.

It may be noted that, as opposed to the clip 130 (FIGS. 3A–D), wherein both cutting element 133 and counter element 136 are movable relative to their respective rings 22 and 12, in the clip 140 only cutting element 152 is movable relative to ring portion 142, while counter element 162 does not move relative to ring portion 144.

Figure 4E:
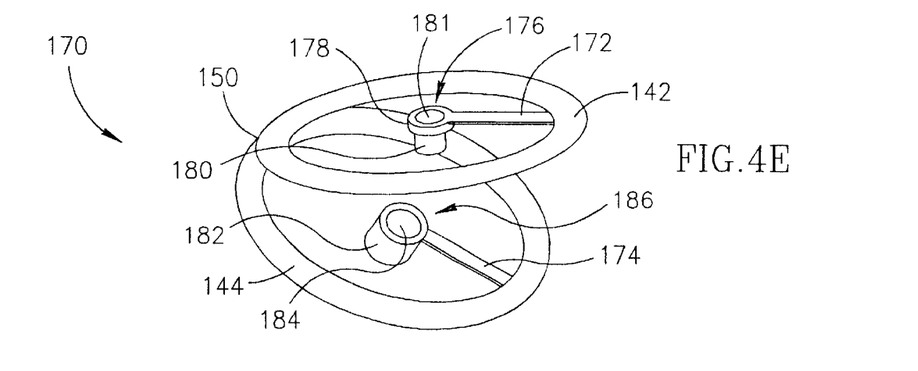
FIG. 4E is a pictorial view of a surgical clip according to a fifth embodiment of the present invention, the clip being in an open configuration.

FIG. 4E illustrates a surgical clip according to a fifth embodiment of the present invention. Clip 170 is similar to clip 140 (FIGS. 4A, 4B, 4C, 4D) in that it includes an intermediate portion 150 formed of a shape memory alloy and is provided with ring portions 142 and 144. However, ring portions 142 and 144 are provided with respective arms 172, 174 which extend from corresponding points along ring portions 142, 144 into the interior thereof. Arms 172, 174 may be fastened to respective ring portions 142, 144 by any suitable means. On the end of arm 172 there is formed a cutting element 176 having a head portion 178 and a cylindrical portion 180 having an aperture 181. The end of arm 174 is provided with a counter element 186 having a cylindrical portion 182 and a cylindrical aperture 184 of size and configuration similar to that of cylindrical portion 180 of cutting element 176.

Figure 5A:
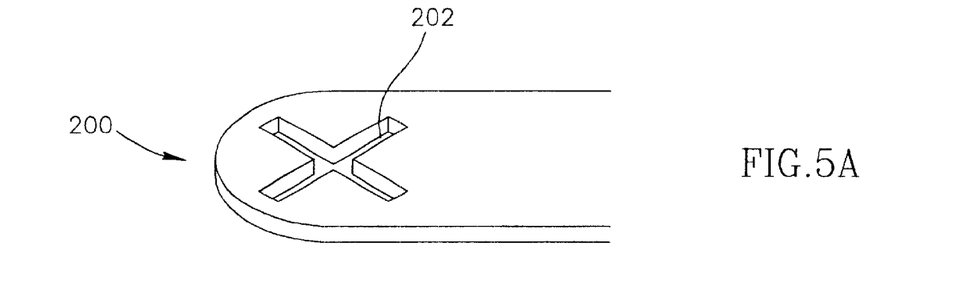
FIGS. 5A and 5B are pictorial illustrations of respective counter and cutting elements which may be employed in the surgical clip according to the embodiment shown in FIG. 4E.
Figure 5B:
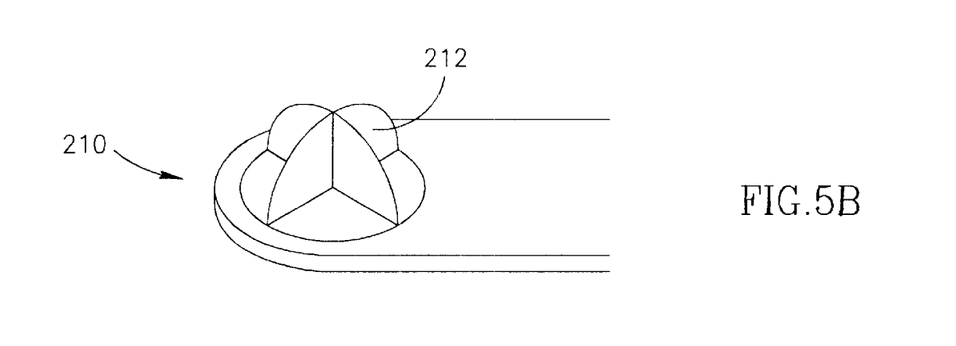

In FIG. 4E, intermediate portion 150 of clip 170 is shown in a plastic state, wherein the ring portions 142 and 144 have been moved apart. When, however, intermediate portion 150 of clip 170 is in an elastic state (not shown), ring portions 142 and 144 are firmly pressed against each other, and cylindrical portion 178 of cutting element 176 is positioned adjacent aperture 184 of counter element 186. By applying pressure to head portion 178 of cutting element 176 on arm 172 and to cylindrical portion 182 of counter element 186, cylindrical portion 180 of cutting element 176 is forced into aperture 184, where it is held in position by the snug fit between cylindrical portion 180 and the inner surface of aperture 184. FIGS. 5A and 5B are pictorial illustrations of a counter element, referenced generally 200, and of a cutting element, referenced generally 210, which may be employed in the surgical clip 170 shown in FIG. 4E. Counter element 200 is provided with an X-shaped aperture 202 which corresponds in configuration and size to blade 212 of cutting element 210. Thus, when employing counter element 200 and cutting element 210 in the device of the present invention, when the intermediate portion of the clip is in an elastic state, as discussed above, counter element 200 and cutting element 210 may be pressed together, thus forcing blade 212 into aperture 202.

Figure 5C:
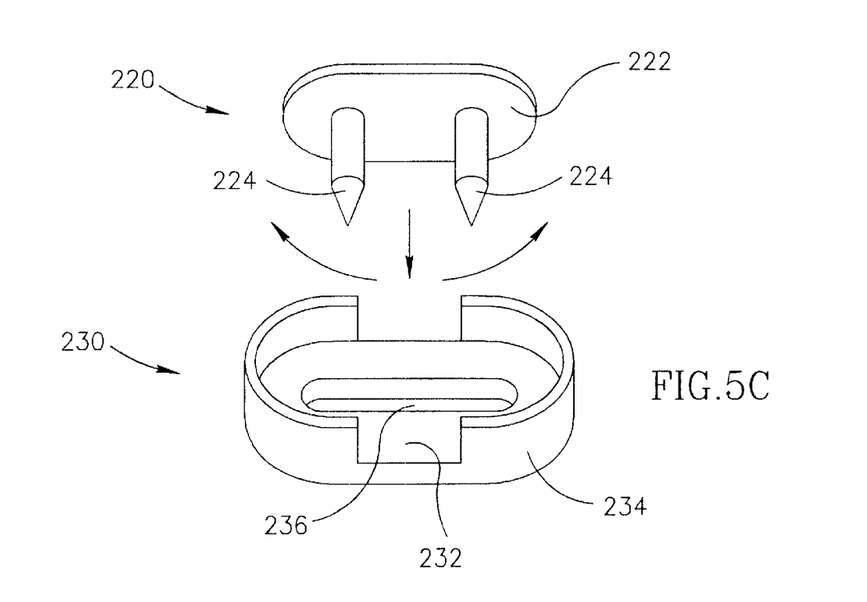
FIG. 5C is a pictorial illustration of a cutting element and a corresponding counter element which may be employed in the surgical clip according to either of FIGS. 1A and 1B.

A further embodiment of the present invention is illustrated in FIG. 5C, which shows a cutting element 220 and a corresponding counter element 230 which may be employed in the surgical clip according to either of FIGS. 1A and 1B. Cutting element 220 is provided with an elliptically shaped base portion 222 having a pair of needle-like blades 224 protruding therefrom. Counter element 230 is provided with an elliptically shaped base portion 232, similar in configuration and size to base portion 222 of cutting element 220, and a flange 234 extending therefrom. Base portion 232 also has an elliptical aperture 236, whose width is similar to that of blades 224 and whose length is at least equal to the distance between the outer edge of one blade to the outer edge of the other blade. Thus, when employing counter element 230 and cutting element 220 in the device of the present invention, when the intermediate portion of the clip is in an elastic state, as discussed above, counter element 230 and cutting element 220 are pressed together, thus forcing blades 224 into aperture 236.

Figure 5D:
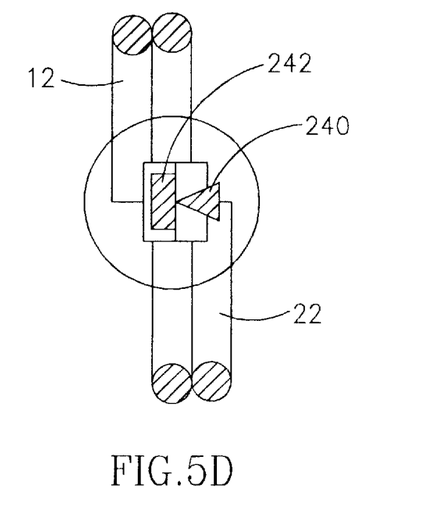
FIG. 5D is a pictorial illustration of a surgical clip in accordance with the present invention, wherein a further embodiment of a cutting element and counter element are employed.
Figure 5E:
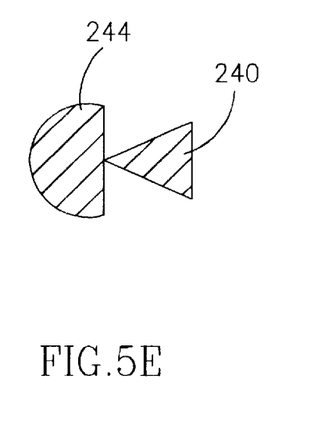
FIGS. 5E, 5F, 5G, 5H, and 5I are further alternative embodiments of cutting elements and counter elements which may be employed in the surgical clip according to the present invention.
Figure 5F:
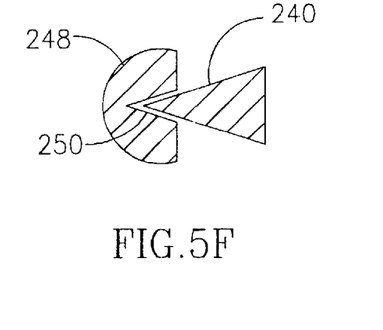
Figure 5G:
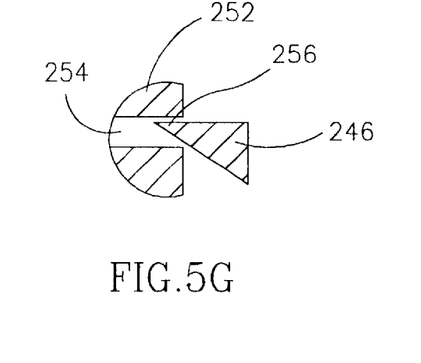
Figure 5H:
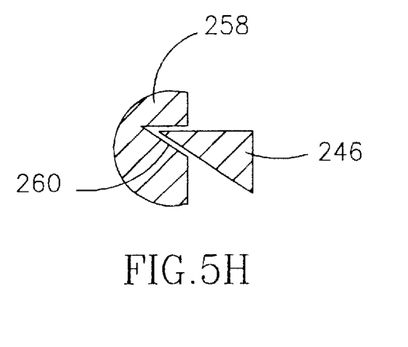
Figure 5I:
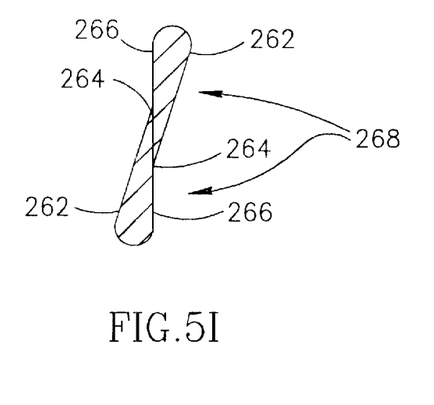

FIGS. 5D, 5E, 5F, 5G, 5H, and 5I illustrate several particular examples of the relationship between specific blade element and counter element combinations, which may replace the blade elements and counter element employed in the embodiments of the present invention shown in FIGS. 2–4. As shown in FIG. 5D, when the shape memory alloy of the device is in an elastic state, loops 12 and 22 are pressed against each other. FIGS. 5D and 5E show blade 240 when it has made contact with each of the flat-surfaced counter elements 242 and 244. In FIG. 5F there are shown a blade 240 and a counter element 248 having a recess 250 shaped to accommodate the tip of blade 240. FIG. 5G shows a blade 246 and a counter element 252 having a cylindrical recess 254 extending therethrough. Recess 254 is large enough to receive the tip 256 of blade 246. However, if blade 246 is moved further into recess 254, its movement will be stopped when it has reached the point at which the width of blade 246 which has entered recess 254 is equal to the width of recess 254. In FIG. 5H, there is provided a counter element 258 having a triangular recess 260 shaped to accommodate the tip of blade 246. FIG. 5I shows an alternative embodiment, wherein the blade element and counter element combination has been replaced by a pair of blade elements 268 in the form of blades 262 which come into contact, when loops 12 and 22 (FIG. 5D) are pressed against each other, such that the tip 264 of each blade 262 lies along a side 266 of the other blade 262.

FIGS. 6A–D show a surgical clip 300 according to a sixth embodiment of the present invention. Clip 300 includes two ring portions 302, 304, which are attached at an intermediate portion 306 formed of a shape memory alloy. Ring portion 302 is provided with an off-center crossbar 308 having a rotatable blade element 310 thereon. Cutting element 310 includes a blade 312 and a head portion 314 by means of which the blade 312 may be rotated downward toward the center of ring portion 302. Across the center of ring 304 there is provided a counter element 316 configured as a pair of parallel bars 318 having a generally rectangular gap 320 therebetween. Bars 318 are positioned such that gap 320 is wide enough to accommodate blade 312, yet narrow enough to provide a snug fit therefor. It will be appreciated by persons skilled in the art that counter element 316 may be replaced by any other counter element suitable for use with cutting blade 312.

Figure 6A:
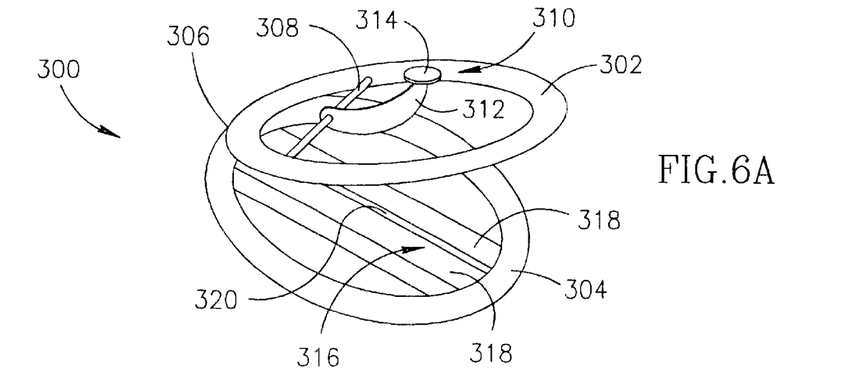
FIG. 6A is a pictorial illustration of a surgical clip according to a sixth embodiment of the present invention.
Figure 6B:
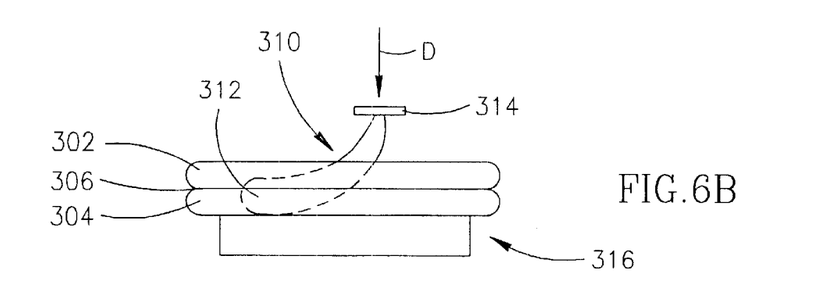
FIG. 6B is a side view illustration of the surgical clip shown in FIG. 6A, the clip being in a closed configuration.
Figure 6C:
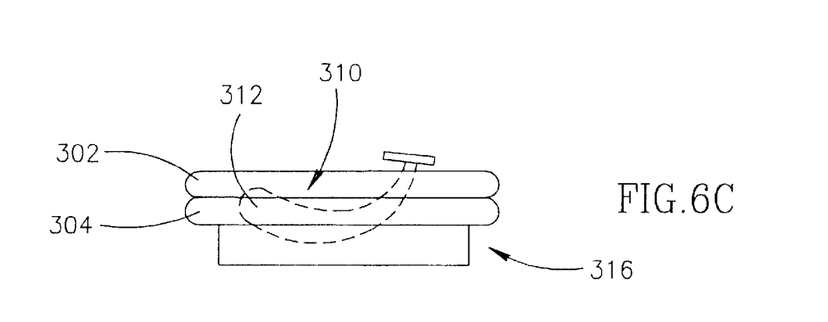
FIGS. 6C, and 6D are side view illustrations of the surgical clip shown in FIG. 6A, the clip being in a closed position, wherein the cutting element is being pressed into cutting engagement with the counter element and wherein the cutting element has been released from cutting engagement with the counter element, respectively.
Figure 6D:
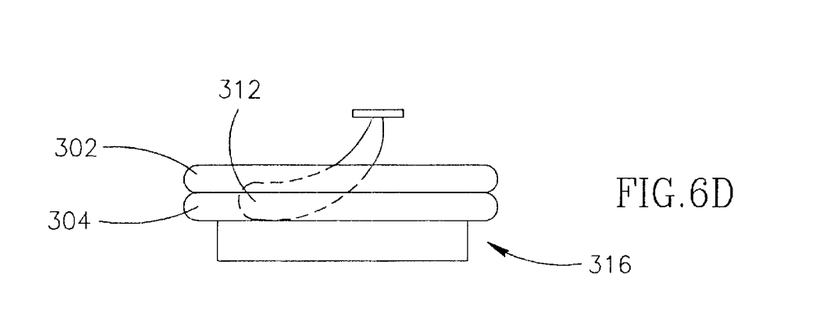

When intermediate portion 306 is in a plastic state, ring portions 203 and 304 may be moved apart, as to the position shown in FIG. 6A. When, however, as shown in FIGS. 6B–D, intermediate portion 306 of the clip 300 is in an elastic state, ring portions 302 and 304 are firmly pressed against each other. As shown in FIG. 6B, by applying pressure in the general direction of arrow D to head portion 314 of cutting element 310, blade 312 is rotated about crossbar 308, such that it moves downward, in the sense of FIG. 6B. This will result in the cutting element 310 being in the position shown in FIG. 6C, wherein blade 312 is snugly fit within gap 320 of counter element 316. If desired, the cutting element 310 may be provided with biasing or similar means (not shown), whereby the blade 312 is pulled or pushed out of gap 320 so that it is automatically returned to its upper position, as shown in FIG. 6D.

With reference to FIGS. 7A–D, there are shown portions 52 and 54 of a hollow organ 50, which it is desired to join together by anastomosis. Hollow organ 50 may be a colon, or any other hollow organ which requires anastomosis. Alternatively, the method of the present invention may be employed for the connection of a portion of a first hollow organ to a second hollow organ, such as the connection of a colon portion to a stomach. The method of the present invention will now be described with reference to clip 10. However, it will be appreciated by persons skilled in the art that the method of the present invention may be carried out by utilizing any embodiment of the clip, or by employing any of the elements described above, in accordance with the present invention.

Additionally, it will be appreciated by persons skilled in the art that a device employing a shape memory alloy, such as a clip according to the present invention, may be described as being of one of two different types. A first type of device employs a shape memory alloy which is in an easily deformable, martensitic state when it is cooled to below room temperature, which achieves a fully or partial austenitic state at room temperature, and which is in a completely austenitic state when heated to at least its upper phase transition temperature, which is somewhere between room temperature and body temperature. According to the second type of device, the shape memory alloy is in an easily deformable, martensitic state at room temperature, whereat the device is deformed and applied, and the shape memory alloy achieves a completely austenitic state when heated to above room temperature. The difference between the two types of devices is in the temperature range at which the shape memory alloy is easily deformable. Thus, by utilizing a device including a shape memory alloy of the second type, allows more freedom in application. The method of the present invention discussed hereinbelow will be described with regard to a device of the first type.

Referring again to FIGS. 7A–D, at least the shape memory alloy portion 13 of clip 10 is cooled to at least its lower phase transition temperature, whereat the shape memory alloy is in its martensitic state, as known in the art, the intermediate portion 13 of clip 10 thus being in a plastic state. The lower phase transition temperature may be generally any temperature above −273° C., although more generally it is approximately 25–35° C. below body temperature, preferably approximately 0° C. Loops 12 and 22 are manually moved apart a desired distance and clip 10 is preserved in the cooled state for as long as required until insertion into the organ 50.

Open ends 56 and 58 of separate organ portions 52 and 54 are surgically stapled or sewn closed, as by sutures 72, thereby resulting in separate closed ends 56a and 58a. Portions 52 and 54 of organ 50 are drawn together in an adjacent, side-by-side relationship, and adjacent walls 60 and 62 are perforated at punctures 64 and 66, respectively, the punctures 64 and 66 being adjacent. The size and shape of punctures 64 and 66 are chosen as desired, so as to be able to facilitate positioning of loops 12 and 22 inside respective organ portion 52 and 54. Clip 10 is introduced into organ portions 52 and 54 by inserting loops 12 and 22 via punctures 64 and 66, respectively, such that loops 12 and 22 are situated inside organ portions 52 and 54, so as to straddle respective walls 60 and 62. While the method of the present invention is described herein in relation to FIGS. 7A–D, wherein both organ portions 52 and 54 are first surgically stapled or sewn closed, it will be understood by persons skilled in the art that either one or both of the organ portions 52 and 54 may be sewn closed after insertion of the surgical clip, without departing from the scope of the invention.

The relative positions of portions 52 and 54 of organ 50 and the relative position of clip 10 in relation thereto must be maintained for a period of time during which the temperature of organ 50 is effective to cause the temperature of the intermediate portion 13 of the clip 10 to rise to a temperature at least equal to its upper phase transition temperature, whereat the clip 10 achieves its austenitic state, which is, preferably, below body temperature. During the time that the temperature of the intermediate portion 13 of the clip 10 rises towards its transition temperature, loops 12 and 22 continue to converge and to press the tissue portions 68 and 70 of organ walls 60 and 62 located therebetween more and more tightly against each other. Tissue portions 68 and 70 are defined by the portions of respective walls 60 and 62 located between loops 12 and 22. Thus, each of tissue portions 68 and 70 is configured as an area similar in shape and size to the loops 12 and 22 of clip 10.

The rate by which the temperature of intermediate portion 13 of clip 10 rises may be accelerated by heating clip 10, for example, by any method known in the art.

Figure 7A:
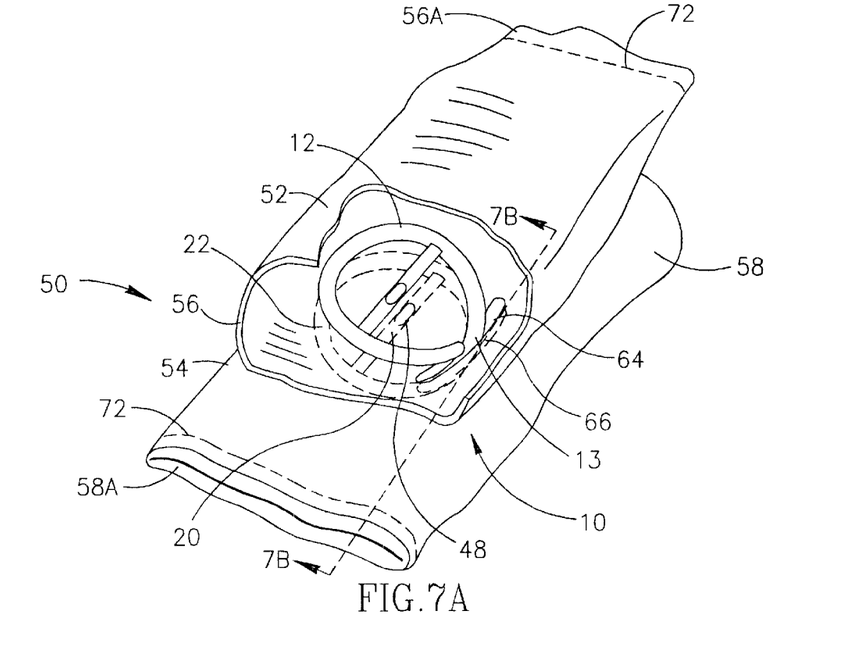
FIG. 7A is a pictorial illustration of a hollow organ inside which there has been placed the surgical clip of FIGS. 1A and 1B, in accordance with the present invention, the surgical clip being in a plastic state.
Figure 7B:
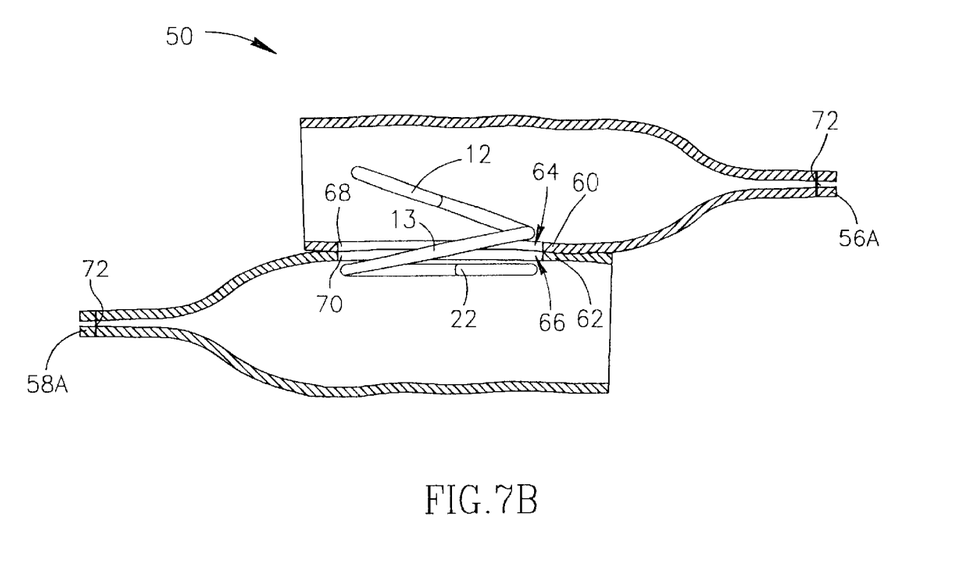
FIG. 7B is a cross-sectional view, taken in the direction of line 7B—7B, of the hollow organ and surgical clip shown in FIG. 7A.
Figure 7C:
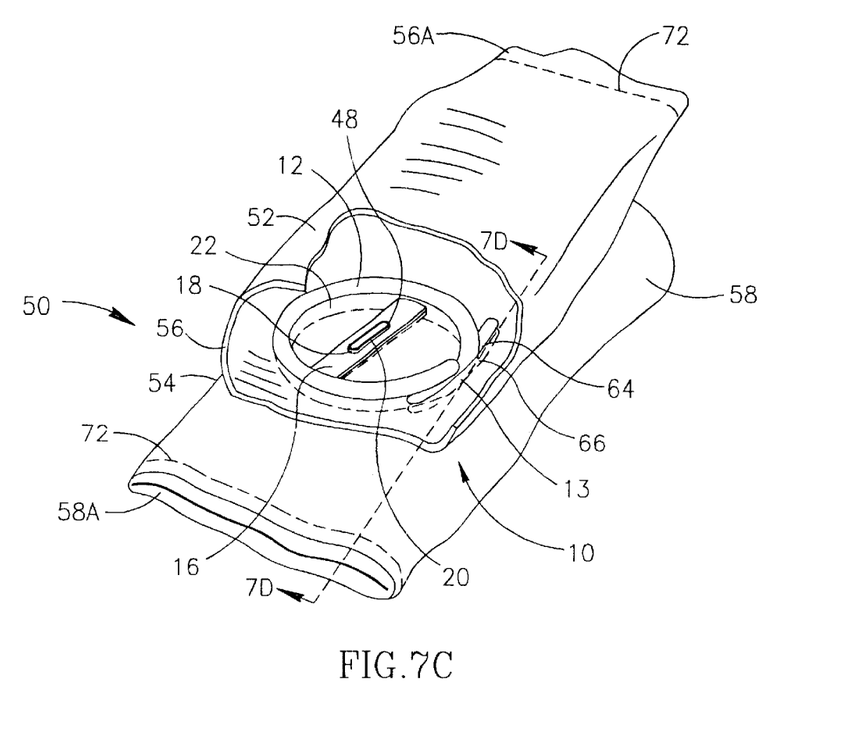
FIG. 7C is a view of the hollow organ and surgical clip shown in FIG. 7A, the surgical clip being in an elastic state.
Figure 7D:
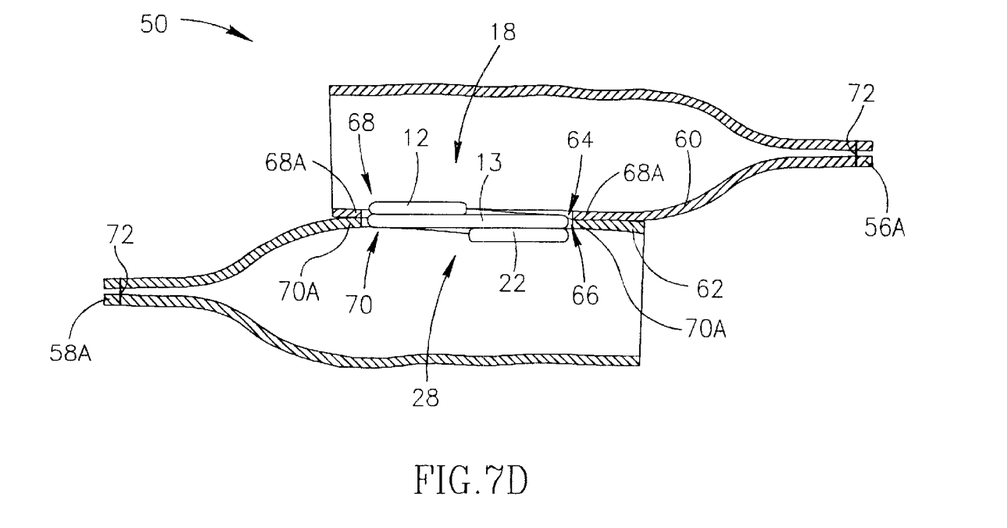
FIG. 7D is a cross-sectional view, taken in the direction of line 7D—7D, of the hollow organ and surgical clip shown in FIG. 7C.

Once the temperature of the intermediate portion 13 of clip 10 has risen above its transition temperature, clip 10 has returned to its elastic phase, as shown in FIGS. 7C and 7D, wherein loops 12 and 22 are pressing against each other, and thus maintains walls 60 and 62 in fixed position relative to each other. At the same time, blade 48 of cutting element 20 is being pressed into aperture 18, thus slicing out a portion of tissue portions 68 and 70 which is similar in size and shape to that of blade 48. This slicing out of a portion of the tissue will create initial patency of the gastrointestinal tract.

It will be appreciated by persons skilled in the art that, if another embodiment of the present invention were employed, such as clip 130 of FIGS. 3A–D, wherein the cutting element 33 and counter-element 136 are actuatable by external manual pressure, such pressure may be provided by any means known in the art, such as by use of an instrument (not shown) designed for this purpose.

After a portion of the tissue has been sliced out of tissue portions 68 and 70, the only pathway from portion 52 to portion 54 of organ 50 is via aperture 18 on crossbar 16 and aperture 28 of cutting element 20.

Due to the pressure exerted by clip 10 on walls 60 and 62 of organ 50, respective tissue portions 68 and 70 are pressed so tightly against each other that blood flow to these tissue portions ceases, resulting in eventual necrosis of these tissue portions 68 and 70. As tissue 68 and 70 die, the tissue portions 68a and 70a immediately thereoutside mend together such that portions 52 and 54 of organ 50 are joined, and organ 50 may function as one continuous organ. Once tissue portions 68 and 70 die, they, together with clip 10, become separated from walls 62 and 60, resulting in a hole 74 (FIG. 7C). Dead tissue portions 70 and 68, together with clip 10 are passed out of organ 50, via hole 74, by the normal activity of the organ. For example, if organ 50 is the small intestine, and the direction of peristalsis is from portion 52 towards portion 54, then clip 10 and tissue portions 70 and 68 will be passed through portion 54 by the normal activity of the small intestine.

It will be appreciated by persons skilled in the art that, if desired, instead of employing clip 10 in the surgical procedure as discussed above, and as illustrated in FIGS. 7A–D, either of clips 140 and 170 may be employed. The use of either of these embodiments of the present invention would require that, after a clip (140, 170) has been introduced into the organ 50 and the intermediate portion thereof has attained its elastic (martensitic) state, as discussed above, the respective cutting element (152, 176) and counter element (162, 186) would have to be manually forced into cutting engagement. This would cause the cutting element (152, 176), together with the counter element (162, 186), to slice out a portion of the tissues located therebetween, the size and shape of the tissue sliced out being similar in size and shape to that of the cylindrical portion (158, 180). This slicing out of a portion of the tissue will create initial patency of the gastrointestinal tract.

Alternatively, if desired, any of clips 110, 130, and 300 may be employed in the surgical procedure discussed above. The use of clip 110 would enable the blade 128 and crossbar 116 to automatically make an incision through the portions of the tissue located therebetween, as the blade 128 is forced into cutting engagement with the crossbar 116 when the clip 110 is in an elastic state, as discussed above with regard to FIGS. 2A–B. The use of either of clips 130 and 300 would require that, after the clip (130, 300) has been introduced into the organ 50 and has attained its elastic state, as discussed above, the respective cutting element (133, 310) and counter element (136, 316) would have to be manually forced into cutting engagement. This would cause the cutting element (133, 310), together with the counter element (136, 316), to make an incision through the portions of the tissue located therebetween. This incision through a portion of the tissue will create initial patency of the gastrointestinal tract. If desired, after an incision has been made by any of the clips (110, 130, 300), the incision may be widened somewhat, although should not be widened to the entire area of the tissue portions 68 and 70.

It will be appreciated by persons skilled in the art that there is a direct relationship between the size and shape of the clip used in the surgical procedure described above and the size and shape of the resulting hole in the organ. It is thus possible to chose to perform the procedure with a clip of a particular size and shape so as to achieve a hole of a desired size and shape.

It will be appreciated by persons skilled in the art that the present invention is not limited by what has been shown and described hereinabove, merely by way of illustrative example. Rather, the scope of the present invention is limited solely by the claims, which follow:

What is claimed is:

1. A surgical clip formed at least partly of a shape memory alloy, said clip including:
    a first length of a wire defining a closed geometrical shape having a central opening;
    a second length of a wire defining a closed geometrical shape similar in configuration and magnitude to that of said first length of wire, wherein, when placed in side-by-side registration, said first and second lengths of wire fully overlap;
    an intermediate portion located between said first length of wire and said second length of wire, said intermediate portion formed of a shape memory alloy;
    a cutting element associated with said first length of wire;
    a counter element associated with said second length of wire and arranged for cutting engagement with said cutting element;
    wherein when at a first temperature or higher, said first and second lengths of wire are positioned in a side-by-side closed position and said shape memory alloy is in an elastic state, and further, when at a second temperature or lower, below said first temperature, said shape memory alloy is in a plastic state, thereby enabling said first and second lengths of wire to be moved into and to retain a spaced apart position, and upon heating of said clip to a temperature at least equal to said first temperature, said first and second lengths of wire return to said side-by-side closed position, thereby to apply a compressive force to tissue located therebetween.

2. The surgical clip according to claim 1, further including apparatus for pressing said cutting element into cutting engagement with said counter element wherein, when at said first temperature or higher, said apparatus for pressing presses said cutting element into cutting engagement with said counter element.

3. The surgical clip according to claim 1, further including apparatus for pressing said cutting element into cutting engagement with said counter element wherein, when at said first temperature or higher, said apparatus for pressing is actuatable by an outside force.

4. The surgical clip according to claim 1, wherein said geometrical shape is a circle.

5. The surgical clip according to claim 1, wherein said geometrical shape is an ellipse.

6. The surgical clip according to claim 1, wherein said first length of wire and said second length of wire are defined by a continuous coil.

7. The surgical clip according to claim 1, wherein said first length of wire and said second length of wire are two distinct lengths of wire, each defining a closed geometrical shape.

8. The surgical clip according to claim 1, wherein said counter element also includes a cutting element.

9. A method for anastomosing a gastrointestinal tract, said method including the following steps:
 (a) providing a surgical clip formed at least partly of a shape memory alloy, the clip including:
   a first length of a wire defining a closed geometrical shape having a central opening;
   a second length of a wire defining a closed geometrical shape similar in configuration and magnitude to that of the first length of wire, wherein, when placed in side-by-side registration, the first and second lengths of wire fully overlap;
   an intermediate portion located between said first length of wire and said second length of wire, said intermediate portion formed of a shape memory alloy;
   a cutting element associated with the first length of wire;
   a counter element associated with the second length of wire and arranged for cutting engagement with the cutting element;
 (b) cooling at least the intermediate portion to a temperature below a lower phase transition temperature thereof, whereat the intermediate portion is in a plastic state, thereby enabling the first and second lengths of wire to be moved into and to retain a spaced apart position;
 (c) manually moving apart the first and second lengths of wire;
 (d) drawing together portions of the gastrointestinal tract wherein anastomosis is desired, such that the portions are in adjacent, side-by-side relationship, at least one of the portions being open-ended;
 (e) surgically sealing the open ends of the portions of the gastrointestinal tract;
 (f) forming punctures in walls of the gastrointestinal tract adjacent to each other, the puncture being adjacent;
 (g) introducing the clip through the punctures, such that the a wall of each portion of the gastrointestinal tract is situated between the first and second lengths of wire;
 (h) maintaining the relative positions of the portions of the gastrointestinal tract and the clip in relation thereto, while raising the temperature of at least the intermediate portion to a temperature above its upper phase transition temperature, whereat the intermediate portion is in an elastic state, thereby causing the first and second lengths of wire to attain the side-by-side registration, thereby to apply a compressive force to tissue located therebetween.

10. A method according to claim 9, the clip further including apparatus for pressing the cutting element into cutting engagement with the counter element wherein, when at said upper phase transition temperature or higher, the apparatus for pressing presses the cutting element into cutting engagement with the counter element, thereby creating initial patency of the gastrointestinal tract.

11. A method according to claim 9, the clip further including apparatus for pressing the cutting element into cutting engagement with the counter element, wherein, after step (h) said method further includes the step of pressing the cutting element into cutting engagement with the counter element, thereby creating initial patency of the gastrointestinal tract.

12. A method for anastomosing a gastrointestinal tract according to claim 9, wherein in said step (h), the temperature of the clip is raised to the temperature above its upper phase transition temperature by the heat of the gastrointestinal tract.

13. A method according to claim 9, the clip further including apparatus for pressing the cutting element into cutting engagement with the counter element wherein, when at said upper phase transition temperature or higher, the apparatus for pressing presses the cutting element into cutting engagement with the counter element, thereby creating an opening in the tissue located between the first and second lengths of wire, thereby creating initial patency of the gastrointestinal tract; and
 said method including, after step (h), the additional step of widening the opening.

* * * * *